US00PP19499P2

(12) United States Plant Patent
Zornig

(10) Patent No.: US PP19,499 P2
(45) Date of Patent: Nov. 25, 2008

(54) *GUZMANIA* PLANT NAMED 'ORION'

(50) Latin Name: ***Guzmania* hybrid**
Varietal Denomination: Orion

(75) Inventor: Rolf Kurt Zornig, Sao Paulo (BR)

(73) Assignee: Altria-Lab Plants LLC, Homestead, FL (US)

( * ) Notice: Subject to any disclaimer, the term of this patent is extended or adjusted under 35 U.S.C. 154(b) by 0 days.

(21) Appl. No.: 12/011,386

(22) Filed: Jan. 25, 2008

(51) Int. Cl.
*A01H 5/00* (2006.01)

(52) U.S. Cl. ..... Plt./371

(58) Field of Classification Search ..... Plt./371
See application file for complete search history.

*Primary Examiner*—Annette H Para
(74) *Attorney, Agent, or Firm*—C. A. Whealy

(57) ABSTRACT

A new and distinct cultivar of *Guzmania* plant named 'Orion', characterized by its compact, upright and outwardly arching growth habit; dark green-colored foliage; inflorescences held upright and above foliage on strong scapes; inflorescences with red purple-colored primary bracts; and long-lasting inflorescences that maintain good coloration for about three months in the interiorscape and about 14 to 16 weeks in the greenhouse.

1 Drawing Sheet

Botanical designation: *Guzmania* hybrid.
Cultivar denomination: 'Orion'.

BACKGROUND OF THE INVENTION

The present invention relates a new and distinct cultivar of *Guzmania,* botanically known as *Guzmania* hybrid and hereinafter referred to by the name 'Orion'.

The new *Guzmania* is a product of a planned breeding program conducted by the Inventor in Sao Paulo, Brazil. The objective of the breeding program is to create new *Guzmania* varieties having unique flower colors and enhanced postproduction longevity.

The new *Guzmania* originated from a cross-pollination made by the Inventor in January, 2000, in Sao Paulo, Brazil, of an unnamed proprietary selection of *Guzmania* hybrid, not patented, as the female, or seed, parent with unnamed proprietary selection of *Guzmania lingulata,* not patented, as the male, or pollen, parent. The new *Guzmania* was discovered and selected by the Inventor as a flowering plant within the progeny of the stated cross-pollination in a controlled environment in Sao Brazil, in September, 2004.

Asexual reproduction of the new *Guzmania* by tissue culture in a controlled environment in Homestead, Fla., has shown that the unique features of this new *Guzmania* are stable and reproduced true to type in successive generations.

SUMMARY OF THE INVENTION

The cultivar Orion has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Orion'. These characteristics in combination distinguish 'Orion' as a new and distinct cultivar of *Guzmania:*

1. Compact, upright and outwardly arching growth habit.
2. Dark green-colored foliage.

3. Inflorescences held upright and above foliage on strong scapes.
4. Inflorescences with red purple-colored primary bracts.
5. Long-lasting inflorescences that maintain good coloration for about three months in the interiorscape and about 14 to 16 weeks in the greenhouse.

Plants of the new *Guzmania* can be compared to plants of the female parent selection in the following characteristics:

1. Plants of the new *Guzmania* have larger inflorescences than plants of the female parent selection.
2. Plants of the new *Guzmania* and female parent selection differ in primary bract color as plants of the female parent selection have purple-colored primary bracts.
3. Inflorescences of plants of the new *Guzmania* last about six weeks longer than inflorescences of plants of the female parent selection.

Plants of the new *Guzmania* can be compared to plants of the male parent selection primarily in primary bract color as plants of the male parent selection have white-colored primary bracts.

Plants of the new *Guzmania* can be compared to plants of the *Guzmania* cultivar Ultra, disclosed in U.S. Plant Pat. No. 8,221. In side-by-side comparisons conducted in Homestead, Fla., plants of the new *Guzmania* and the cultivar Ultra differed in the following characteristics:

1. Plants of the new *Guzmania* had larger inflorescences than plants of the cultivar Ultra.
2. Plants of the new *Guzmania* and the cultivar Ultra differed in primary bract color as plants of the cultivar Ultra had paler red purple-colored flowers bracts.
3. Inflorescences of plants of the new *Guzmania* lasted two to three weeks longer than inflorescences of plants of the cultivar Ultra.

Plants of the new *Guzmania* can be compared to plants of the *Guzmania* cultivar Tempo, disclosed in U.S. Plant Pat. No. 12,124. In side-by-side comparisons conducted in Homestead, Fla., plants of the new *Guzmania* and the cultivar Tempo differed in the following characteristics:

1. Leaves of plants of the new *Guzmania* were broader and darker green in color than leaves of plants of the cultivar Tempo.

2. Plants of the new *Guzmania* had larger inflorescences than plants of the cultivar Tempo.
3. Plants of the new *Guzmania* and the cultivar Tempo differed in primary bract color as plants of the cultivar Tempo had red purple and white-colored flowers bracts.

BRIEF DESCRIPTION OF THE PHOTOGRAPHS

The accompanying colored photographs illustrate the overall appearance of the new *Guzmania,* showing the colors as true as it is reasonably possible to obtain in colored reproductions of this type. Colors in the photographs may differ slightly from the color values cited in the detailed botanical description which accurately describe the colors of the new *Guzmania.*

The photograph at the bottom of the sheet comprises a side perspective view of a typical flowering plant of 'Orion' grown in a container.

The photograph at the top of the sheet is a close-up view of a typical inflorescence of 'Orion'.

DETAILED BOTANICAL DESCRIPTION

All color references are measured against The Royal Horticultural Society Colour Chart, 1995 Edition. Colors and numerical measurements are approximate as plant growth and development depends on environmental conditions and cultural practices such as light level and temperature, among others, without, however any variance in genotype.

Plants used for the aforementioned photographs and the following description were about 40 weeks old and grown in containers in Homestead, Fla., during the spring and summer in a polyethylene-covered greenhouse with day temperatures averaging 28° C., night temperatures averaging 20° C. and light levels about 1,600 foot-candles.

Botanical classification: *Guzmania* hybrid cultivar Orion.

Parentage:

*Female, or seed, parent.*—Unnamed proprietary selection of *Guzmania* hybrid, not patented.

*Male, or pollen, parent.*—Unnamed proprietary selection of *Guzmania lingulata,* not patented.

Propagation:

*Type.*—By tissue culture.

*Time to initiate roots on tissue-cultured plants.*—Summer: About 14 days at temperatures of 29° C. Winter: About 20 days at temperatures of 24° C.

*Time to produce a rooted tissue-cultured plant.*—Summer: About 110 days at 29° C. Winter: About 130 days at 24° C.

*Root description.*—Thin, fibrous; brownish with white-colored apices.

*Rooting habit.*—Freely branching; moderately dense.

Plant description:

*General appearance.*—Compact, upright and outwardly arching plant habit. Basal rosette of outwardly curved strap-like leaves affixed in tight spiral ranks around a very short central stem. Terminal inflorescence on an upright scape which emerges from the center of the basal rosette.

*Plant height, soil surface to top of inflorescence.*—About 22 cm.

*Plant diameter or spread.*—About 52 cm.

*Stem length.*—About 12 cm.

*Stem diameter.*—About 8 mm.

*Stem color.*—157B.

Foliage description:

*Arrangement.*—Basal rosette, spiral phyllotaxis; sessile. Quantity of leaves per plant: Plants typically produce about 16 to 18 leaves prior to inflorescence development.

*Shape.*—Ligulate.

*Apex.*—Acuminate.

*Margin.*—Entire.

*Length.*—About 35 cm.

*Width (flattened).*—About 2.7 cm.

*Aspect.*—Leaves curved outward over their length and downward towards the apex.

*Texture, upper and lower surfaces.*—Leathery, stiff; smooth, glabrous.

*Venation.*—Parallel.

*Leaf sheath.*—Not observed.

*Color.*—Developing leaves, upper and lower surfaces: 146A. Fully expanded leaves, upper surface: 147A; venation, 147A. Fully expanded leaves, lower surface: 147B; venation, 147B.

Inflorescence description:

*Inflorescence form.*—Terminal inflorescences with showy primary bracts; inflorescences supported on erect and strong scapes.

*Fragrance.*—None detected.

*Inflorescence longevity.*—Inflorescences of the new *Guzmania* are very long-lasting; bract coloration is maintained for about three months in an interior-scape and about 14 to 16 weeks in the greenhouse. Inflorescences persistent.

*Natural flowering season and time to flower.*—Plants of the new *Guzmania* typically flower in the spring or summer.

*Flowers.*—Flower development has not been observed on plants of the new *Guzmania.*

*Bracts.*—Only primary (flower) bracts observed; terminal (fertile) bracts and scape bracts not observed. Quantity per flower spike, primary bracts: About 18. Shape, primary bracts: Ligulate, apices, acuminate; margins, entire. Length, primary bracts: About 11.5 cm. Width, primary bracts: About 3 cm. Texture, primary bracts, upper and lower surfaces: Leathery; stiff; smooth, glabrous. Color: Primary bracts, upper surface: 71A. Primary bracts, lower surface: 71A.

*Scape.*—Strength: Strong. Aspect: Typically erect. Length: About 20 cm. Diameter: About 1 cm. Texture: Smooth, glabrous. Color: Close to 145D.

Temperature tolerance: Plants of the new *Guzmania* have been observed to tolerate temperatures from about 6° C. to about 41° C.

Disease/pest resistance: Plants of the new *Guzmania* have not been observed to resistant to pathogens and pests common to *Guzmania.*

It is claimed:

1. A new and distinct *Guzmania* plant named 'Orion' as illustrated and described.

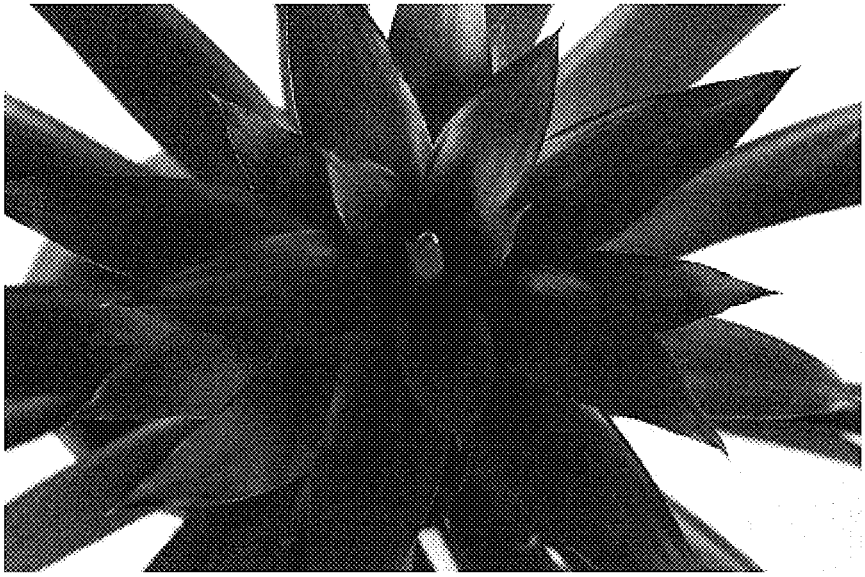
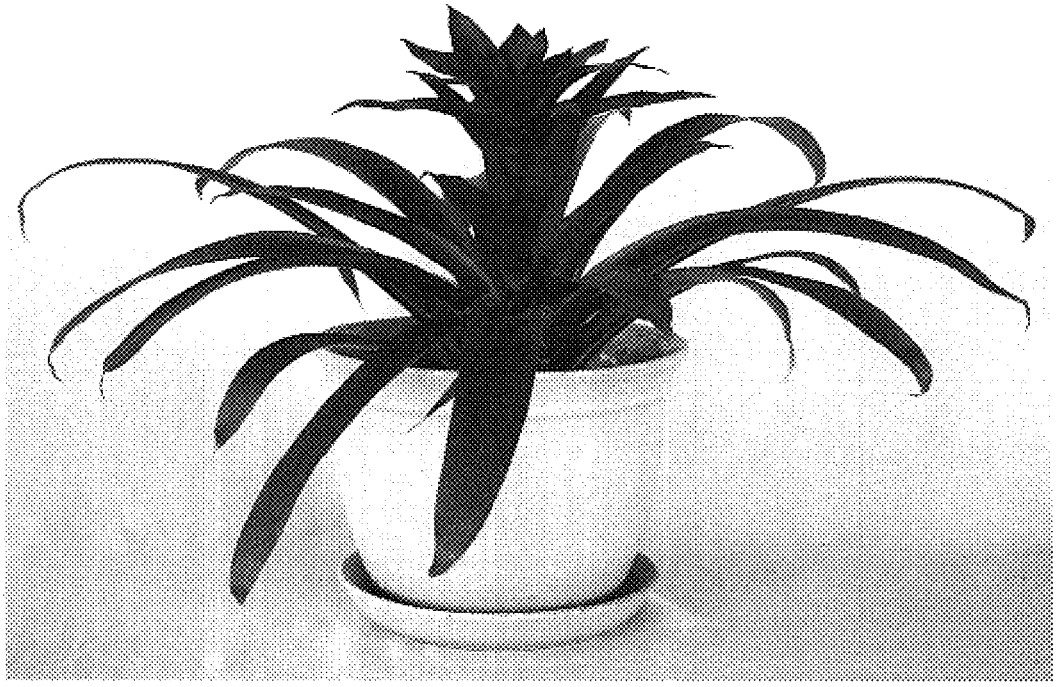

* * * * *